(12) United States Patent
Lee et al.

(10) Patent No.: US 8,372,604 B2
(45) Date of Patent: *Feb. 12, 2013

(54) COMPOSITIONS AND METHODS FOR REVERSE TRANSCRIPTASE-POLYMERASE CHAIN REACTION (RT-PCR)

(75) Inventors: Jun Lee, San Diego, CA (US); Ayoub Rashtchian, Gaithersburg, MD (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/981,240

(22) Filed: Dec. 29, 2010

(65) Prior Publication Data

US 2011/0217735 A1 Sep. 8, 2011

Related U.S. Application Data

(63) Continuation of application No. 10/861,469, filed on Jun. 7, 2004, now Pat. No. 7,883,871, which is a continuation of application No. 10/224,334, filed on Aug. 21, 2002, now Pat. No. 6,767,724, which is a continuation of application No. 09/472,066, filed on Dec. 23, 1999, now Pat. No. 6,495,350, which is a continuation of application No. 09/054,485, filed on Apr. 3, 1998, now abandoned.

(60) Provisional application No. 60/042,629, filed on Apr. 3, 1997.

(51) Int. Cl.
*C12P 19/34* (2006.01)

(52) U.S. Cl. .................. 435/91.2; 435/91.21

(58) Field of Classification Search ............ 435/91.2, 435/91.21
See application file for complete search history.

(56) References Cited

U.S. PATENT DOCUMENTS

| | | |
|---|---|---|
| 4,683,202 A | 7/1987 | Mullis |
| 5,244,797 A | 9/1993 | Kotewicz et al. |
| 5,310,652 A | 5/1994 | Gelfand et al. |
| 5,322,770 A | 6/1994 | Gelfand |
| 5,405,776 A | 4/1995 | Kotewicz et al. |
| 5,407,800 A | 4/1995 | Gelfand et al. |
| 5,512,445 A | 4/1996 | Yang et al. |
| 5,556,772 A | 9/1996 | Sorge et al. |
| 5,561,058 A | 10/1996 | Gelfand et al. |
| 5,618,702 A | 4/1997 | Scanlon |
| 5,618,703 A | 4/1997 | Gelfand et al. |
| 5,618,711 A | 4/1997 | Gelfand et al. |
| 5,624,833 A | 4/1997 | Gelfand et al. |
| 5,641,864 A | 6/1997 | Gelfand |
| 5,693,517 A | 12/1997 | Gelfand et al. |
| 6,060,240 A | 5/2000 | Kamb et al. |
| 6,495,350 B1 | 12/2002 | Lee et al. |
| 6,518,019 B2 | 2/2003 | Gerard et al. |
| 6,589,768 B1 | 7/2003 | Kotewicz et al. |
| 6,610,522 B1 | 8/2003 | Kotewicz et al. |
| 6,630,333 B1 | 10/2003 | Hughes, Jr. |
| 6,835,561 B1 | 12/2004 | Gerard et al. |
| 6,989,259 B2 | 1/2006 | Gerard et al. |
| 7,074,556 B2 | 7/2006 | Li et al. |
| 7,078,208 B2 | 7/2006 | Smith et al. |

FOREIGN PATENT DOCUMENTS

| | | |
|---|---|---|
| EP | 0502588 A2 | 9/1992 |
| EP | 0736608 A1 | 10/1996 |
| EP | 0791650 A1 | 8/1997 |
| WO | 97/24455 A2 | 7/1997 |
| WO | 98/44161 A1 | 10/1998 |

OTHER PUBLICATIONS

Gibc-BRL catalog (1993-1994). pp. 1-2.*
Aatinski, J T. et al., "A coupled One-Step Reverse Transcription PCR Procedure for Generation of Full-Length Open Reading Frames", *BioTechniques*, 16 Eaton Publishing Co., 1994, 282-288.
Aatsinki, J. T. , "Coupled One-Step Reverse Transcription and Polymerase Chain Reaction Procedure for Cloning Large cDNA Fragments", *PCR Cloning Protocols From Molecular Cloning to Genetic Engineering*, White, B.A.. ed., Humana Press, Totowa, NJ, Feb. 1997, 55-60.
Allain, B et al., "CIS Elements and Trans-acting Factors required for Minus Strand DNA Transfer during Reverse Transcription of the Genomic RNA of Murine Leukemia Virus", *J. Mol. Biol.*, 277, Mar. 1998, 225-235.
Ando, T. et al., "A One-Tube Method of Reverse Transcription-PCR to efficiently Amplify a 3-kilobase Region From the RNA Polymerase Gene to the Poly(A) Tail of small Round-structured Viruses(Norwalk-Like Viruses)", *J. Clin. Microbiol.*, 35, American Society for Microbiology, Mar. 1997, 570-577.
Basu, Subhalakshmi et al., "Sulphydryl groups in the template-primer-binding domain of murine leukemia virus reverse transcriptase", *Biochem. J.*, vol. 296, 1993, 577-583.
Ben-Artzi, H. et al., "Characterization of the double stranded RNA dependent RNAse activity associated with recombinant reverse transcriptases", *Nucl. Acids Res.*, 20, Oxford University Press, 1992, 5115-5118.
Blain, S. et al., "Differential Effects of Moloney Murine Leukemia Virus Reverse Transcriptase Mutations on RNase H Activity in Mg2+ and Mn2+", *The Journal of Biological Chemistry*, vol. 271, 1996, 1448-1454.

(Continued)

*Primary Examiner* — Gary Benzion
*Assistant Examiner* — Cynthia Wilder

(57) ABSTRACT

The present invention is directed to compositions and methods useful for the amplification of nucleic acid molecules by reverse transcriptase-polymerase chain reaction (RT-PCR). Specifically, the invention provides compositions and methods for the amplification of nucleic acid molecules in a simplified one- or two-step RT-PCR procedure using combinations of reverse transcriptase and thermostable DNA polymerase enzymes in conjunction with sulfur-containing molecules or acetate-containing molecules (or combinations of such sulfur-containing molecules and acetate-containing molecules), and optionally bovine serum albumin. The invention thus facilitates the rapid and efficient amplification of nucleic acid molecules and the detection and quantitation of RNA molecules. The invention also is useful in the rapid production and amplification of cDNAs which may be used for a variety of industrial, medical and forensic purposes.

14 Claims, 7 Drawing Sheets

OTHER PUBLICATIONS

Blain, S. W. et al., "Effects on DNA Synthesis and Translocation Caused by Mutations in the RNAse H Domain of Moloney Murine Luekemia Virus Reverse Transcriptase", *J. Virol.*, 69, The American society for Microbiology, 1995, 4440-4452.

Casas, I et al., "Two Different PCR Assays to Detect Enteroviral RNA in CSF Samples from Patients with Acute Aseptic Meningitis", *J. Med. Virol.*, 47, Wiley-Liss, Inc, 1995, 378-385.

Chowdhury, K et al., "Elucidation of the Role of Arg 110 of Murine Leukemia Virus Reverse Transcriptase in the Catalytic Mechanism: Biochemical Characterization of Its Mutant Enzymes", *Biochemistry*, 35, American Chemical Society, 1996, 16610-16620.

Don, et al., "A One tube reaction for synthesis and amplification of total cDNA from small numbers of cells", *Nucleic Acids Research* vol. 21 (3), 1993, 783.

Dudding, L R. et al., "Analysis of the RNA- and DNA-Dependent DNA Polymerase Activities of Point Mutants of HIV-1 Reverse Transcriptase Lacking Ribonclease H Activity", *Biochemistry*, 30 American Chemical Society, 1991, 10498-10506.

EP06012490.6, "European Search Report", mailed Nov. 27, 2006, 14 pages.

EP06012490.6, "European Search Report", mailed Aug. 25, 2006, 7 pages.

EP10178653.1 "Extended European Search Report", mailed Jul. 11, 2011, 12 pages.

EP98917984.1, "European Search Report", mailed Feb. 10, 2004, 4 pages.

Gao, G. et al., "Conferring RNA polymerase Activity to a DNA polymerase: A single residue in reverse transcriptase controls substrate selection", *Proceedings of the National Academy of Sciences (PNAS)*, 94, National Academy of Sciences of the USA, Jan. 1997, 407-411.

Gao, G. et al., "Replication Defect of Moloney Murine Leukemia Virus with a Mutant Reverse Transcriptase That Can Incorporate Ribonucleotides and Deoxyribonucleotides", *J. Virol.*, 72, American Society for Microbiology, Jul. 1998, 5905-5911.

Gao, H. Q. et al., "Similarities and Differences in the RNase H Activities of Human Immunodeficiency Virus Type 1 Reverse Transcriptase and Moloney Murine Leukemia Virus Reverse Transcriptase", *J. Mol. Biol.*, 294, Dec. 1999, 1097-1113.

Georgiadis, M. M. et al., "Mechanistic implications from the Structure of a Catalytic Fragment of Moloney Murine Leukemia Virus Reverse Transcriptase", *Structure*, 3, Current Biology Ltd., 1995, 879-892

Gerard, Gary F. et al., "cDNA Synthesis by Cloned Moloney Murine Leukemia Virus Reverse Transcriptase Lacking RNase H Activity", *Focus*, vol. 11, No. 4, Life Technologies, Inc., 1989, 66-69.

Gerard, Gary F. et al., "cDNA Synthesis by Moloney Murine Leukemia Virus RNase H-Minus Reverse Transcriptase Possessing Full DNA Polymerase Activity", *Focus*, vol. 14, No. 3, 1992, 91-93.

Gerard, Gary F. et al., "Ch 6: Reverse Transcriptase (EC 2.7.7.49): The Use of Cloned Moloney Murine Leukemia Virus Reverse Transcriptase to Synthesize DNA from RNA", *Methods in Molecular Biology*, vol. 16, Humana Press, Totowa, NJ, Enzymes of Molecular Biology, 1993, 73-93.

Gerard, Gary F. , "Reverse Transcriptase: A Historical Perspective", *Focus*, vol. 20, No. 3, Origin Publishing Ltd., 1998, 65-67.

Gibson, K. et al., "Detection of HIV-1 in serum, using reverse transcription and the polymerase chain reaction (RT-PCR)", *Journal of Virological Methods, Elsevier BV*, NL, vol. 43, No. 1., Jun. 1, 1993, 103-104.

Goblet, C. et al., "One-step amplification of transcripts in total RNA using the polymerase chain reaction", *Nucl. Acids Res.*, 17, IRL Press at Oxford University Press, 1989, 2144.

Goedken, E. R. et al., "Folding the Ribonuclease H Domain of Moloney Murine Leukemia Virus Reverse Transcriptase Requires Metal Binding or a Short N-terminal Extension", *Proteins: Structure, Function, and Genetics*, 33, Wiley-Liss, Inc., Oct. 1998, 135-143.

Goff, S. et al., "Isolation and Properties of Moloney Murine Leukemia Virus Mutants: Use of a Rapid Assay for Release of Virion Reverse Transcriptase", *J. Virol.*, 38, American Society for Microbiology, 1981, 239-248.

Goff, S. P. , "Retroviral Reverse Transcriptase: Synthesis, Structure, and Function", *J. Acquired Immune Deficiency Syndromes*, 3, Raven Press, Ltd, 1990, 817-831.

Gouvea, V. et al., "Polymerase Chain Reaction Amplification and Typing of Rotavirus Nucleic Acid from Stool Specimens", *J. Clin. Microbiol.*, 28, American Society for Microbiology, 1990, 276-282.

Guo, J. et al., "Defects in Primer-Template Binding, Processive DNA Synthesis, and RNAse H Activity Associated with Chimeric Reverse Transcriptases Having the Murine Leukemia Virus Polymerase Domain Joined to *Escherichia coli* RNAse H", *Biochemistry*, 34, American Chemical Society, 1995, 5018-5029.

Hizi, A. et al., "Mutational Analysis of the Ribonuclease H Activity of Human Immunodeficiency Virus 1 Reverse Transcriptase", *Virol.*, 175, Academic Press, 1990, 575-580.

Invitrogen, , "cDNA Sysnthesis System", *GIBCO BRL Product Catalogue and Reference Guide*, Life Technologies, Inc., 1995-1996, 12-18.

Invitrogen, , "Systems for Cloning", *Gibco-BRL catalog*, 1993-1994, 11-12.

Jin, J. et al., "Analysis of the Role of Glutamine 190 in the Catalytic Mechanism of Murine Transcriptase", *The Journal of Biological Chemistry*, 274 American Molecular Biology, Jul. 1999, 20861-20868.

Jo, et al., "Cytotoxic Actions of Cytokines on Cultured Mouse Luteal Cells are Independent of Nitric Oxide", *Journal of Steroid Biochemistry and Molecular Biology*, Elsevier Science Ltd., XP005348949, ISSN: 0960-0760, Dec. 1995, pp. 291-296.

Johnson, M. S. et al., "Computer analysis of retroviral pol genes: assignment of enzymatic functions to specific sequences and homologies with nonviral enzymes", *Proceedings of the National Academy of Sciences (PNAS)*, vol. 83(20) National Academy of Sciences, 1986, 7648-7652.

Kanaya, S. et al., "Identification of the Amino Acid Residues Involved in an Active Site of *Escherichia coli* Ribonuclease H by Site-directed Mutagenesis", *The Journal of Biological Chemistry*, 265, The American Society for Biochemistry and Molecular Biology, 1990, 4615-4621.

Kaushik, N. et al., "Tyrosine 222, a member of the YXDD motif of MuLV RT, is catalytically essential and is a major component of the fidelity center", *Biochemistry*, vol. 38, 1999, 2617-2627.

Kelleher, C D. et al., "Characterization of RNA Strand Displacement Synthesis by Moloney Murine Leukemia Virus Reverse Transcriptase", *The Journal of Biological Chemistry*, 273, The American Society for Biochemistry and Molecular Biology, Inc., Apr. 1998, 9976-9986.

Kokko, H I. et al., "Single-Step Immunocapture RT-PCR in the Detection of Raspberry Bushy Dwearf Virus", *BioTechniques*, 20, Eaton Publishing Co., May 1996, 842-846.

Kotewicz, Michael L. et al., "Isolation of cloned Moloney murine leukemia virus reverse transcriptase lacking ribonuclease H activity", *Nucleic Acids Research*, vol. 16, No. 1, 1988, 265-277.

Krug, M. S. et al., "First-Strand cDNA Synthesis Primed with Oligo(dT)", *Methods in Enzymology* vol. 152: *Guide to Molecular Cloning Techniques*, Academic Press, Inc., 1987, 316-325.

Lavignon, M. et al., "Inhibition of Moloney Murine Leukemia Virus Reverse Transcriptase by alpha-Anomeric Oligonucleotides", *Biochem. Biophys. Res. Commun.*, 161, Academic Press, Inc., 1989, 1184-1990.

Lee, Eui H. et al., "A Highly Sensitive Method for One-Step Amplification of RNA by Polymeraase Chain Reaction", *Focus*, vol. 19, No. 2, Life Technologies, Inc., 1997, 39-42.

Levin, H. L. , "An Unusual Mechanism of Self-Primed Reverse Transcription Requires the RNase H Domain of Reverse Transcriptase to Cleave an RNA Duplex", *Mol. Cell. Biol.*, 16, American Society for Microbiology, Oct. 1996, 5645-5654.

Levin, H. L. , "It's Prime Time for Reverse Transcriptase", *Cell*, 88, Cell Press, Jan. 1997, 5-8.

Loya, S. et al., "The Interaction of Illimaquinone, a Selective Inhibitor of the RNase H Activity, with the Reverse Transcriptases of Human Immunodeficiency and Murine Leukemia Retroviruses", *The Journal of Biological Chemistry*, 268, The American Society for Biochemistry and Molecular Bilology , Inc., 1993, 9323-9328.

Mallet, F. et al., "Continuous RT-PCR Using AMV-RT and RT Taq DNA Polymerase: Characterization and Comparison to Uncoupled Procedures", *BioTechniques*, 18, Eaton publishing Co, 1995, 678-687.

McClelland, et al., "KGB : a single buffer for all restriction endonucleases", *Nucleic Acids Research* vol. 16 (1), 1988, 364.

Messer, L. I. et al., "Functional Analysis of Reverse Transcription by a Frameshift pol Mutant of Murine Leukemia Virus", *Virology*, 146, Academic Press, 1985, 146-152.

Misra, Hari S. et al., "An Enzymatically Active Chimeric HIV-1 Reverse Transcriptase (RT) with the RNase-H Domain of Murine Leukemia Virus RT Exists as a Monomer", *The Journal of Biological Chemistry*, vol. 273, No. 16, Apr. 17, 1998, 9785-9789.

Mizrahi, Valerie et al., "Site-directed mutagenesis of the conserved Asp-443 and Asp-498 carboxy-terminal residues of HIV-1 reverse transcriptase", *Nucleic Acids Research*, vol. 18(18), Oxford University Press, 1990, 5359-5363.

Myers, Thomas W. et al., "Reverse Transcription and DNA Amplification by a *Thermus thermophilus* DNA Polymerase", *Biochemistry*, vol. 30, No. 31, American Chemical Society, Aug. 6, 1991, 7661-7666.

Nathan, M. et al., "Optimizing Long RT-PCR", *Focus*, 17, Life Technologies, 1995, 78-80.

Oefelein, et al., "Molecular Detection of Prostate Epithelial Cells from the surgical Field and Peripheral Circulation during Radical Prostatectomy", *Journal of Urology*, vol. 155, No. 1, XP005576766, Jan. 1996, 238-242.

Olive, D. M. et al., "Polymerase Chain Reaction Assay for Detection of Human Cytomegalovirus", *J. Clin. Microbiol.*, 27, American Society for Microbiology, 1989, 1238-1242.

Onel, et al., "Molecular and Cellular Biology", 15(10), Oct. 1995, 5329-5338.

Payan, C. et al., "Detection of Hepatitis C Virus RNA by a Reliable, Optimized Single-Step Reverese Transcription Polymerase Chain Reaction", *Res. Virol.*, 146, Elsevier Science, 1995, 363-370.

PCT/US1998/006581, , "International Search Report", mailed Aug. 24, 1998, 3 pages.

Post, K et al., "A Large Deletion in the Connection Subdomain of Murine Leukemia Virus Reverse Transcriptase or Replacement of the RNase H Domain with *Escherichia coli* RNase H Results in Altered Polymerase and RNase H Activities", *Biochemistry*, vol. 32(21), American Chemical Society, 1993, 5508-5517.

Repaske, R et al., "Inhibition of RNase H Activity and Viral Replication by Single Mutations in the 3' Region of Moloney Murine Leukemia Virus Reverse Transcriptase", *J. Virol*, 63, The American society for Microbiology, 1989, 1460-1464.

Roche Diagnostics Corporation, , "Titan TM one Tube RT-PCR System", *Boehringer Mannheim Online Catalog* http://biochem.roche.com/pack-insert/1855476B.pdf, Roche Diagnostics Corporation, Jun. 19, 1999.

Schultz, S. J. et al., "Polypurine Tract Primer Generation and Utilization by Moloney Murine Leukemia Virus Reverse Transcriptase", *The Journal of Biological Chemistry*, 274 American Society for Biochemistry and Molecular Biology, Dec. 1999, 34547-34555.

Sellner, L. N. et al., "Reverse transcripts inhibits Taq polymerase activity", *Nucleic Acids Research*, vol. 20, No. 7, 1992, 1487-1490.

Shirasawa, Y et al., "Transdominant Inhibition of Moloney Murine Leukemia Virus Proliferation by Defective Mutants of Reverse Transcriptase", *J. Biochem.*, 119, The Japanese Biochemical Society, Jun. 1996, 1070-1075.

Tanese, N. et al., "Abortive Reverse Transcription by Mutants of Moloney Murine Leukemia Virus Deficient in the Reverse Transcriptase-Associated RNase H Function", *J. Virol.*, 65, American Society for Microbiology, 1991, 4387-4397.

Telesnitsky, A. et al., "RNase H Domain Mutations Affect the Interaction Between Moloney Murine Leukemia Virus Reverse Transcriptase and Its Primer-Template", *Proceedings of the National Academy of Sciences (PNAS)*, 90, National Academy of Sciences, 1993, 1276-1280.

Tosh, C. et al., "One-tube and One-buffer System of RT-PCR Amplification of ID Gene of Foot- and- Mouth Disease Virus Field Isolates", *Acta Virol*, 41, Slovak Academic Press Ltd., Jun. 1997, 153-155.

Umlauft, et al., *J.Clinical Microbiology* ; 34 (10), 1996, 2552-2558.

Vanhee-Brossollet, Christine et al., "A natural antisense RNA derived from the HIV-1 env gene encodes a protein which is recognised by circulating antibodies of HIV<+> individuals", *Virology*, vol. 206, No. 1, XP004786641, Elsevier Inc, Jan. 10, 1995, 196-202.

Wang, Rong-Fu et al., "A Simplified Single Tube, Single Buffer System for RNA-PCR", *BioTechniques*, vol. 12, No. 5, Eaton Publishing Co., May 1992, 702, 704.

Whiting, S. H. et al., "Properties of Strand Displacement Synthesis by Moloney Murine Leukemia Virus Reverse Transcriptase: Mechanistic Implications", *J. Mol. Biol.*, 278, Academic Press Limited, May 1998, 559-577.

Whorl, B. M. et al., "Footprint Analysis of Replicating Murine Leukemia Virus Reverse Transcriptase", *Science*, 267, American Association for the Advancement of Science, Jan. 6, 1995, 96-99.

Zannettino, Andrew et al., "A Powerful New Technique for Isolating Genes Encoding Cell Surface Antigens Using Retroviral Expression Cloning", *Journal of Immunology*, vol. 156, Jan. 1996, 611-620.

Zoelch, Claudia et al., "Titan One Tube RT-PCR System: Performance and Ease of Use in RT-PCR", *Biochemica*, Jun. 6, 1999, 1-11.

* cited by examiner

COMPOSITIONS AND METHODS FOR REVERSE TRANSCRIPTASE-POLYMERASE CHAIN REACTION (RT-PCR)

CROSS REFERENCE TO RELATED APPLICATION

This application is a continuation of U.S. application Ser. No. 10/861,469 (pending), filed Jun. 7, 2004; which is a continuation of U.S. application Ser. No. 10/224,334 (now U.S. Pat. No. 6,767,724), filed Aug. 21, 2002; which is a continuation of U.S. application Ser. No. 09/472,066 (now U.S. Pat. No. 6,495,350), filed Dec. 23, 1999; which is a continuation of U.S. application Ser. No. 09/054,485 (abandoned), filed Apr. 3, 1998; which claims the benefit of priority from U.S. Provisional Application No. 60/042,629, filed Apr. 3, 1997 (the entire contents of which are incorporated herein by reference in their entireties).

FIELD OF THE INVENTION

The present invention is in the fields of molecular and cellular biology. The invention is particularly directed to compositions and methods useful for the amplification of nucleic acid molecules by reverse transcriptase-polymerase chain reaction (RT-PCR). Specifically, the invention provides compositions and methods for the amplification of nucleic acid molecules in a simplified one- or two-step RT-PCR procedure using combinations of reverse transcriptase and thermostable. DNA polymerase enzymes in conjunction with sulfur-containing molecules or acetate-containing molecules (or combinations of sulfur-containing molecules and acetate-containing molecules) and optionally bovine serum albumin. The invention thus facilitates the rapid and efficient amplification of nucleic acid molecules and the detection and quantitation of RNA molecules. The invention also is useful in the rapid production and amplification of cDNAs (single-stranded and double-stranded) which may be used for a variety of industrial, medical and forensic purposes.

BACKGROUND OF THE INVENTION

Reverse Transcription of RNA

The term "reverse transcriptase" describes a class of polymerases characterized as RNA-dependent DNA polymerases. All known reverse transcriptases require a primer to synthesize a DNA transcript from an RNA template. Historically, reverse transcriptase has been used primarily to transcribe mRNA into cDNA which can then be cloned into a vector for further manipulation.

Avian myoblastosis virus (AMV) reverse transcriptase was the first widely used RNA-dependent DNA polymerase (Verma, *Biochim. Biophys. Acta* 473:1 (1977)). The enzyme has 5'-3' RNA-directed DNA polymerase activity, 5'-3' DNA-directed DNA polymerase activity, and RNase H activity. RNase H is a processive 5' and 3' ribonuclease, specific for the RNA strand for RNA-DNA hybrids (Perbal, *A Practical Guide to Molecular Cloning*, New York: Wiley & Sons (1984)). Errors in transcription cannot be corrected by reverse transcriptase because known viral reverse transcriptases lack the 3'→5' exonuclease activity necessary for proofreading (Saunders and Saunders, *Microbial Genetics Applied to Biotechnology*, London: Croom Helm (1987)). A detailed study of the activity of AMV reverse transcriptase and its associated RNase H activity has been presented by Berger et al., *Biochemistry* 22:2365-2372 (1983).

Another reverse transcriptase which is used extensively in molecular biology is reverse transcriptase originating from Moloney murine leukemia virus (M-MLV). See, e.g., Gerard, G. R., *DNA* 5:271-279 (1986) and Kotewicz, M. L., et al., *Gene* 35:249-258 (1985). M-MLV reverse transcriptase substantially lacking in RNase H activity has also been described. See, e.g., U.S. Pat. No. 5,244,797.

PCR Amplification of RNA

Reverse transcriptases have been extensively used in reverse transcribing RNA prior to PCR amplification. This method, often referred to as RNA-PCR or RT-PCR, is widely used for detection and quantitation of RNA.

To attempt to address the technical problems often associated with RT-PCR, a number of protocols have been developed taking into account the three basic steps of the procedure: (a) the denaturation of RNA and the hybridization of reverse primer; (b) the synthesis of cDNA; and (c) PCR amplification. In the so-called "uncoupled" RT-PCR procedure (e.g., two-step RT-PCR), reverse transcription is performed as an independent step using the optimal buffer condition for reverse transcriptase activity. Following cDNA synthesis, the reaction is diluted to decrease $MgCl_2$ and deoxyribonucleoside triphosphate (dNTP) concentrations to conditions optimal for Taq DNA Polymerase activity, and PCR is carried out according to standard conditions (see U.S. Pat. Nos. 4,683,195 and 4,683,202). By contrast, "coupled" RT-PCR methods use a common or compromised buffer for reverse transcriptase and Taq DNA Polymerase activities. In one version, the annealing of reverse primer is a separate step preceding the addition of enzymes, which are then added to the single reaction vessel. In another version, the reverse transcriptase activity is a component of the thermostable Tth DNA polymerase. Annealing and cDNA synthesis are performed in the presence of $Mn^{++}$, then PCR is carried out in the presence of $Mg^{++}$ after the removal of $Mn^{++}$ by a chelating agent. Finally, the "continuous" method (e.g., one-step RT-PCR) integrates the three RT-PCR steps into a single continuous reaction that avoids the opening of the reaction tube for component or enzyme addition. Continuous RT-PCR has been described as a single enzyme system using the reverse transcriptase activity of thermostable Taq DNA Polymerase and Tth polymerase and as a two-enzyme system using AMV-RT and Taq DNA Polymerase wherein the initial 65° C. RNA denaturation step was omitted.

Attempts to streamline the process of RT-PCR have not been easy, and several reports have documented an interference between reverse transcriptase and thermostable DNA polymerase Taq when used in combination in a single tube RT-PCR resulting in low sensitivity or lack of results. For example, there has been at least one report of a general inhibition of Taq DNA polymerase when mixed with reverse transcriptases in one-step/one tube RT-PCR mixtures (Sellner, L. N., et al., *Nucl. Acids Res.* 20 (7):1487-1490 (1992)). This same report indicated that the inhibition was not limited to one type of RT: both AMV-RT and M-MLV-RT inhibited Taq DNA polymerase and limited the sensitivity of RT-PCR. Under the reaction conditions used in the Sellner et al. studies (67 mM Tris-HCl, pH 8.8, 17 mM $(NH_4)_2SO_4$, 1 mM β-mercaptoethanol, 6 µM EDTA, 0.2 mg/ml gelatin), the degree of Taq polymerase inhibition was found to increase with increasing RT concentration, up to a ratio of approximately 3 units of RT:2 units of Taq DNA polymerase beyond which Taq polymerase was rendered completely inactive.

Other reports describe attempts to develop conditions for one-step RT-PCR reactions. For example, the use of AMV-RT for one-step RT-PCR in a buffer comprising 10 mM Tris-HCl, (pH 8.3), 50 mM KCl, 1.5 mM $MgCl_2$, and 0.01% gelatin has been reported (Aatsinki, J. T., et al., *BioTechniques* 16 (2): 282-288 (1994)), while another report demonstrated one-step RT-PCR using a composition comprising AMV-RT and Taq DNA polymerase in a buffer consisting of 10 mM Tris-HCl, pH 8.3, 50 mM KCl, 0.01% gelatin and 1.5 mM $MgCl_2$ (Mallet, F., et al., *BioTechniques* 18 (4):678-687 (1995)). Under the reaction conditions used in the latter report, substitution of M-MLV-RT (RNase $H^+$ or RNase $H^-$ forms) for AMV-RT showed the same activity in the continuous RT-PCR reaction.

BRIEF SUMMARY OF THE INVENTION

The present invention is generally directed to compositions and methods useful for one-step/one-tube RT-PCR, preferably using M-MLV-RT, or its RNase H-deficient ("RNase $H^-$") derivatives, in combination with one or more DNA polymerases, preferably in the presence of sulfur-containing molecules or acetate-containing molecules (or combinations of sulfur-containing molecules and acetate-containing molecules) to relieve the inhibition of PCR often observed when using compositions comprising two or more enzymes having reverse transcriptase activity.

In particular, the invention is directed to methods for amplifying a nucleic acid molecule comprising (a) mixing an RNA template with a composition comprising a Moloney murine leukemia virus (M-MLV) reverse transcriptase, which is preferably substantially reduced in RNase H activity and which is most preferably SuperScript I or SuperScript II, in combination with one or more DNA polymerases and one or more sulfur-containing molecules, such as one or more sulfur-containing buffers, wherein the concentration of sulfur is at least 18 mM, to form a mixture; and (b) incubating the mixture under conditions sufficient to amplify a DNA molecule complementary to all or a portion of the RNA template. In a related aspect, the invention is directed to such methods wherein one or more acetate-containing molecules, such as one or more acetate-containing buffers, is substituted for or combined with the one or more sulfur-containing molecules or buffers in step (a) of the above-described methods, wherein the concentration of the one or more acetate-containing molecules is about 1 mM to about 500 mM. In preferred such methods, the DNA polymerases used are thermostable DNA polymerases, and most preferably Tne, Tma, Taq, Pfu, Tth, VENT, DEEPVENT, Pwo, Tfl, or a mutant, variant or derivative thereof; most preferred in this aspect of the invention is Taq DNA polymerase.

In other preferred aspects of the invention, the DNA polymerases may comprise a first DNA polymerase having 3' exonuclease activity, most preferably a DNA polymerase selected from the group consisting of Pfu, Pwo, DEEPVENT, VENT, Tne, Tma, Kod, and mutants, variants and derivatives thereof, and a second DNA polymerase having substantially reduced 3' exonuclease activity, most preferably a DNA polymerase selected from the group consisting of Taq, Tfl, Tth, and mutants, variants and derivatives thereof. In additional preferred aspects of the invention, the unit ratio of the reverse transcriptase to the DNA polymerases is from about 0.2:2 to about 500:2, and in particularly preferred such aspects the ratio is from about 0.5:2 to about 250:2 or greater than about 3:2.

In other preferred aspects of the invention, the concentration of the one or more sulfur-containing molecules is at least 18 mM, and more preferably about 20 mM to about 50 mM. The invention is also directed to such methods wherein the source of the sulfur-containing molecules is a buffer or a sulfur-containing salt which may be ammonium sulfate, magnesium sulfate, TRIS-sulfate, or manganese sulfate, as well as other sulfur-containing buffers and salts that will be familiar to one of ordinary skill.

In other preferred aspects of the invention, the concentration of the one or more acetate-containing molecules is about 1 mM to about 500 mM, and more preferably about 5 mM to about 250 mM, about 10 mM to about 200 mM, about 25 mM to about 150 mM, about 50 mM to about 100 mM, or about 60 mM. The invention is also directed to such methods wherein the source of the acetate-containing molecules is a buffer or an acetate-containing salt which may be ammonium acetate, magnesium acetate, TRIS-acetate, or manganese acetate, as well as other acetate-containing buffers and salts that will be familiar to one of ordinary skill.

The invention is also directed to such methods wherein the mixture further comprises one or more nucleotides, preferably deoxyribonucleoside triphosphates (most preferably dATP, dUTP, dTTP, dGTP or dCTP), dideoxyribonucleoside triphosphates (most preferably ddATP, ddUTP, ddGTP, ddTTP or ddCTP) or derivatives thereof. Such nucleotides may optionally be detectably labeled (e.g. with a radioactive or nonradioactive detectable label).

The invention is also directed to such methods wherein the mixture further comprises one or more oligonucleotide primers, which are preferably an oligo(dT) primers, random primers, arbitrary primers or target-specific primers, and which is more preferably a gene-specific primer.

The invention is also directed to such methods wherein the incubating step comprises (a) incubating the mixture at a temperature (most preferably a temperature from about 35° C. to about 60° C.) and for a time sufficient to make a DNA molecule complementary to all or a portion of the RNA template; and (b) incubating the DNA molecule complementary to the RNA template at a temperature and for a time sufficient to amplify the DNA molecule, preferably via thermocycling, more preferably thermocycling comprising alternating heating and cooling of the mixture sufficient to amplify said DNA molecule, and most preferably thermocycling comprising alternating from a first temperature range of from about 90° C. to about 100° C., to a second temperature range of from about 40° C. to about 75° C., preferably from about 65° C. to about 75° C. In particularly preferred aspects of the invention, the thermocycling is performed greater than 10 times, more preferably greater than 20 times.

The invention is also directed to such methods wherein the amplification is not substantially inhibited.

The invention is also directed to methods for amplifying a nucleic acid molecule comprising (a) mixing an RNA template with a composition comprising a Moloney murine leukemia virus (M-MLV) reverse transcriptase, which is preferably substantially reduced in RNase H activity, in combination with one or more DNA polymerases (most preferably selected from the group consisting of Tne, Tma, Taq, Pfu, Tth, VENT, DEEPVENT, Pwo, Tfl, and mutants, variants and derivatives thereof), one or more sulfur-containing molecules and one or more potassium-containing molecules, to form a mixture; and (b) incubating the mixture under conditions sufficient to amplify a DNA molecule complementary to all or a portion of the RNA template. In a related aspect, the invention is directed to such methods wherein one or more acetate-containing molecules, such as one or more acetate-containing buffers, is substituted for or combined with the one or more sulfur-containing molecules or buffers in step (a) of the above-described methods.

The invention is also directed to methods for amplifying a nucleic acid molecule comprising (a) mixing an RNA template with a composition comprising a Moloney murine leukemic virus (M-MLV) reverse transcriptase and one or more DNA polymerases, wherein the unit ratio of the reverse transcriptase to the DNA polymerases is greater then 3:2, to form a mixture; and (b) incubating the mixture under conditions sufficient to amplify a DNA molecule complementary to all or a portion of the RNA template.

The invention is also directed to compositions comprising a Moloney Murine Leukemic virus (M-MLV) reverse transcriptase, one or more DNA polymerases and one or more sulfur-containing molecules (wherein the sulfur concentration is at least 18 mM) or one or more acetate-containing molecules (wherein the acetate concentration is about 1 mM to about 500 mM), or combinations of one or more sulfur-containing molecules and one or more acetate-containing molecules at the above concentrations.

The invention is also directed to compositions comprising a Moloney Murine Leukemic virus (M-MLV) reverse transcriptase, one or more DNA polymerases, one or more potassium-containing molecules and one or more sulfur-containing molecules (wherein the sulfur concentration is at least 18 mM) or one or more acetate-containing molecules (wherein the acetate concentration is about 1 mM to about 500 mM), or combinations of one or more sulfur-containing molecules and one or more acetate-containing molecules at the above concentrations.

The invention is also directed to compositions comprising a Moloney. Murine leukemic virus (M-MLV) reverse transcriptase and one or more DNA polymerases, wherein the unit ratio of the reverse transcriptase to the DNA polymerases is greater than 3:2.

Other preferred embodiments of the present invention will be apparent to one of ordinary skill in light of the following drawings and description of the invention, and of the claims.

DETAILED DESCRIPTION OF THE INVENTION

Overview

Figure 1:
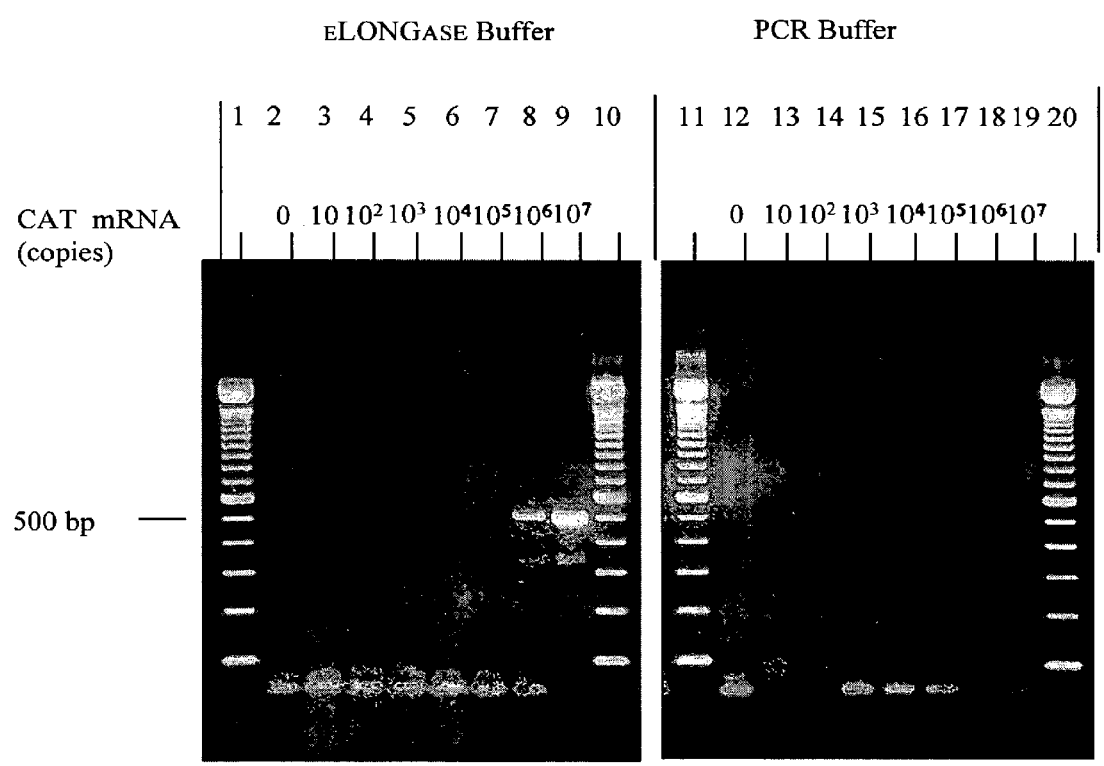
FIG. 1 is a photograph of an ethidium bromide (EtdBr)-stained gel demonstrating the inhibition of RT-PCR by reverse transcriptase. Lanes 1, 10, 11 and 20 contain 100 bp DNA sizing ladders.

The present invention is directed to compositions and methods for use in reverse transcriptase-polymerase chain reaction (RT-PCR) production and analysis of nucleic acids. In particular, the invention provides compositions comprising a variety of components in various combinations. Such components include one or more sulfur-containing molecules or one or more acetate-containing molecules (or combinations of one or more sulfur-containing molecules and one or more acetate-containing molecules), one or more enzymes having reverse transcriptase activity, one or more DNA polymerases, one or more primers, one or more nucleotides and a suitable buffer. These compositions may be used in the methods of the invention to produce, analyze, quantitate and otherwise manipulate nucleic acid molecules using a one- or two-step RT-PCR procedure.

Compositions

The buffer in the compositions of the invention provide appropriate pH and ionic conditions for the enzymes having reverse transcriptase activity and DNA polymerase enzymes. The nucleotides used in the compositions (e.g., deoxyribonucleoside triphosphates (dNTPs)), and the primer nucleic acid molecules provide the substrates for synthesis or amplification of nucleic acid molecules in accordance with the invention. The compositions of the invention may also include inhibition-relieving reagents to assist in overcoming inhibition in RT-PCR reactions.

Buffer and Ionic Conditions

The buffer and ionic conditions of the present compositions have been optimized to relieve RT-mediated inhibition of RT-PCR. Preferred compositions of the invention comprise one or more sulfur-containing molecules, which provide sulfur in ionic form such as sulfate ions, sulfite ions, sulfonate ions (e.g., p-toluenesulfonic acid) and the like. Additional preferred compositions of the invention comprise one or more acetate-containing molecules, or combinations of one or more sulfur-containing molecules and one or more acetate-containing molecules.

The sulfur-containing molecules should be formulated into the compositions to preferably provide a concentration of sulfur in the solution of at least 18 mM, more preferably a concentration of at least 19 mM and most preferably a concentration of at least 20 mM. Particularly preferred concentration ranges for sulfur in the present compositions include about 18 mM to about 500 mM, about 18 mM to about 150 mM, about 18 mM to about 100 mM, about 18 mM to about 75 mM, about 18 mM to about 50 mM or about 18 mM to about 40 mM, and most preferably about 18 mM to about 50 mM.

The sulfur-containing molecules are preferably formulated into the present compositions in the form of one or more salts or buffers. Examples of suitable sulfur-containing salts according to the invention include, but are not limited to, ammonium sulfate, magnesium sulfate, manganese sulfate, potassium sulfate, sodium sulfate and the like. Most preferred are ammonium sulfate, magnesium sulfate and manganese sulfate. Examples of suitable sulfur-containing buffers according to the invention include, but are not limited to, TRIS-sulfate and other sulfuric acid-based buffers, as well as sulfonic acid-based buffers such as AMPSO (3-[(1,1-dimethyl-2-hydroxyethyl)amino]-2-hydroxy-propanesulfonic acid), BES (N,N-bis[2-hydroxyethyl]-2-aminomethanesulfonic acid), MOPS (3-N-morpholino)-propanesulfonic acid), MOPSO (3-N-morpholino)-2-hydroxypropanesulfonic acid, TES (2-{[tris-(hydroxymethyl)-methyl]amino}ethanesulfonic acid), HEPES (N-2-hydroxyethylpiperazine-N'-2-ethansulfonic acid), HEPPS (N-2-hydroxyethylpiperazine-N'-3-propanesulfonic acid), HEPPSO (N-2-hydroxyethylpiperazine-N'-2-hydroxypropanesulfonic acid), TAPS (TES (3-{[tris-(hydroxymethyl)methyl]amino}propanesulfonic acid, CHES (2-(N-cyclohexylamino)ethanesulfonic acid), MES (2-N-morpholino)ethanesulfonic acid, PIPES (piperazine-N,N'-bis-2-ethanesulfonic acid), POPSO (piperazine-N,N'-bis[2-hydroxy]propanesulfonic acid), TAPS(N-tris[hydroxymethyl]methyl-3-aminopropanesulfonic acid), TAPSO (3-[N-tris{hydroxymethyl}methylamino]-2-hydroxypropanesulfonic acid), ACES (N-2-acetamide-2-aminoethane sulfonic acid), DIPSO (3-[N,N-bis(2-hydroxyethyl)amino]-2-hydroxypropanesulfonic acid), CAPSO (3-[cyclohexylamino]-2-hydroxy-1-propanesulfonic acid) and CAPS (3-[cyclohexylamino]propanesulfonic acid). Other sulfur-containing ionic salts and buffers, and other sulfur-containing molecules, suitable for use in the compositions of the invention will be apparent to one of ordinary skill in the art.

The acetate-containing molecules should be formulated into the compositions to preferably provide a concentration of acetate ion in the solution of about 1 mM to about 500 mM. Particularly preferred concentration ranges for acetate ion in the present compositions include about 1 mM to about 500 mM, about 5 mM to about 250 mM, about 10 mM to about 200 mM, about 25 mM to about 150 mM, about 50 mM to about 100 mM, or about 60 mM.

The acetate-containing molecules are preferably formulated into the present compositions in the form of one or more salts or buffers. Examples of suitable acetate-containing salts according to the invention include, but are not limited to, ammonium acetate, magnesium acetate, manganese acetate, potassium acetate, sodium acetate and the like. Examples of suitable acetate-containing buffers according to the invention include, but are not limited to, TRIS-acetate (tris[{hydroxymethyl}]aminomethane]acetate), ADA (N-[2-acetamido]-2-iminodiacetic acid), and imidazole acetate (2-hydroxy-3-[4-imidazolyl]-propionic acid).

In accordance with the invention, one or more potassium-containing molecules may be formulated into the present compositions to substitute for, and thereby reduce the concentration requirement for, sulfur. In this aspect of the invention, the addition of both sulfur-containing molecules and potassium-containing, molecules decreases the concentration requirement for sulfur by about 13-75%, preferably by about 25-50%. For example, when potassium-containing molecules are formulated into the present compositions, the concentration of sulfur-containing molecules may be reduced from about 18 mM to about 2-14 mM, or preferably to about 4-9 mM. It will be understood, of course, that the one or more potassium ions may also be used in the above-described compositions of the invention that contain one or more acetate-containing molecules instead of, or in addition to, the one or more sulfur-containing molecules.

The potassium-containing molecules should be formulated into the compositions at a preferred concentration of at least 2 mM, preferably at least mM, still more preferably at least 10 mM, and most preferably at least 20 mM. Particularly preferred concentration ranges of potassium-containing molecules in the present compositions include about 2 mM to about 500 mM, about 2 mM to about 200 mM, about 2 mM to about 100 mM, about 2 mM to about 75 mM, about 2 mM to about 50 mM, about 2 mM to about 40 mM, about 2 mM to about mM, about 2 mM to about 20 mM and about 2 mM to about 10 mM.

The potassium-containing molecules are preferably formulated into the present compositions in the form of one or more salts or buffers. Examples of suitable potassium salts according to the invention include, but are not limited to, potassium sulfate, potassium sulfite, potassium chloride, potassium nitrate and the like. Most preferred are potassium chloride, potassium sulfate and potassium acetate. Preferred potassium buffers according to the invention include, but are not limited to, potassium phosphate (monobasic), potassium phosphate (dibasic) and the like. Other potassium salts and buffers, and other potassium-containing molecules, suitable for use in the present compositions will be apparent to one of ordinary skill in the art.

Molecules and buffers containing sulfur, acetate or potassium that are suitable for use in the present compositions are available commercially from a wide variety of sources, e.g., from Sigma (St. Louis, Mo.).

Reverse Transcriptase Enzymes

The compositions of the present invention also comprise enzymes having reverse transcriptase activity. According to the present invention, the enzymes having reverse transcriptase activity are Moloney Murine Leukemia Virus (M-MLV) reverse transcriptases. Preferred enzymes for use in the invention include those that are substantially reduced in RNase H activity. By an enzyme "substantially reduced in RNase H activity" is meant that the enzyme has less than about 20%, more preferably less than about 15%, 10% or 5%, and most preferably less than about 2%, of the RNase H activity of a wildtype or RNase H$^+$ enzyme such as wildtype M-MLV reverse transcriptase. The RNase H activity may be determined by a variety of assays, such as those described, for example, in U.S. Pat. No. 5,244,797, in Kotewicz, M. L., et al., *Nucl. Acids Res.* 16:265 (1988) and in Gerard, G. F., et al., *FOCUS* 14 (5):91 (1992), the disclosures of all of which are fully incorporated herein by reference.

Particularly preferred enzymes for use in the invention include, but are not limited to, M-MLV reverse transcriptase (RNase H⁻ or substantially reduced in RNase H activity), and RSV reverse transcriptase (RNase H⁻ or substantially reduced in RNase H activity). Enzymes having reverse transcriptase activity are commercially available (for example, SUPERSCRIPT™, SUPERSCRIPT II™ and M-MLV, available from Life Technologies, Inc.; Rockville, Md.).

DNA Polymerases

The compositions of the invention also comprise one or more DNA polymerases, which are preferably thermostable DNA polymerases. These DNA polymerases may be isolated from natural or recombinant sources, by techniques that are well-known in the art (See WO 92/06200, U.S. Pat. Nos. 5,455,170 and 5,466,591, WO 96/10640 and U.S. patent application Ser. No. 08/370,190, filed Jan. 9, 1995, the disclosures of all of which are incorporated herein by reference), from a variety of thermophilic bacteria that are available commercially (for example, from American Type Culture Collection, Rockville, Md.) or may be obtained by recombinant DNA techniques (see, e.g., WO 96/10640 and U.S. patent application Ser. No. 08/370,190, filed Jan. 9, 1995). Suitable for use as sources of thermostable polymerases or the genes thereof for expression in recombinant systems are the thermophilic bacteria *Thermus thermophilus, Thermococcus lotoralis, Pyrococcus furiosus, Pyrococcus woosii* and other species of the *Pyrococcus* genus, *Bacillus sterothermophilus, Sulfolobus acidocaldarius, Thermoplasma acidophilum, Thermus flavus, Thermus ruber, Thermus brockianus, Thermotoga neapolitana, Thermotoga maritima* and other species of the *Thermotoga* genus, and *Methanobacterium thermoautotrophicum*, and mutants, variants or derivatives thereof. It is to be understood, however, that thermostable DNA polymerases from other organisms may also be used in the present invention without departing from the scope or preferred embodiments thereof. As an alternative to isolation, thermostable DNA polymerases are available commercially from, for example, Life Technologies, Inc. (Rockville, Md.), New England BioLabs (Beverly, Mass.), Finnzymes Oy (Espoo, Finland), Stratagene (La Jolla, Calif.), Boehringer Mannheim Biochemicals (Indianapolis, Ind.) and Perkin Elmer Cetus (Norwalk, Conn.).

Particularly preferred thermostable DNA polymerases for use in the compositions and methods of the present invention include, but are not limited to, Taq, Tne, Tma, Tli/VENT™, DEEPVENT™, Pfu, Pwo, Tfi or Tth DNA polymerases, or mutants or derivatives thereof. Taq DNA polymerase is commercially available, for example from Life Technologies, Inc. (Rockville, Md.), or may be isolated from its natural source, the thermophilic bacterium *Thermus aquaticus*, as described previously (U.S. Pat. Nos. 4,889,818 and 4,965,188). Tne DNA polymerase may be isolated from its natural source, the thermophilic bacterium *Thermotoga neapolitana* (See WO 96/10640 and U.S. patent application Ser. No. 08/370,190, filed Jan. 9, 1995), and Tma DNA polymerase from its natural source, the thermophilic bacterium *Thermotoga maritima* (See U.S. Pat. No. 5,374,553, the disclosure of which is incorporated herein by reference). Methods for producing mutants and derivatives of thermophilic DNA polymerases, particularly of Tne and Tma polymerases, are disclosed in co-pending U.S. patent application Ser. No. 08/689,807 of Deb K. Chatterjee, and in co-pending U.S. patent application Ser. No. 08/689,818 of Deb K. Chatterjee and A. John Hughes, both filed Sep. 6, 1996, which are incorporated by reference herein in their entirety. Tfi, Tli/VENT™ and DEEPVENT™ are available commercially (e.g., from New England BioLabs; Beverly, Mass.), or may be produced as described (Bej, A. K., and Mahbubani, M. H., in: *PCR Technology: Current Innovations*, Griffin, H. G., and Griffin, A. M., eds., CRC Press, pp. 219-237 (1994) for Tli/VENT™; Flaman, J.-M., et al., *Nucl. Acids Res.* 22 (15):3259-3260 (1994) for DEEPVENT™). Thermostable DNA polymerases are preferably added to the present compositions at a final concentration in solution of about 0.1-200 units per milliliter, about 0.1-50 units per milliliter, about 0.1-40 units per milliliter, about 0.1-36 units per milliliter, about 0.1-34 units per milliliter, about 0.1-32 units per milliliter, about 0.1-30 units per milliliter, or about 0.1-20 units per milliliter, and most preferably at a concentration of about 20 units per milliliter.

In preferred compositions of the invention, the concentration of DNA polymerases is determined as a ratio of the concentration of the enzymes having reverse transcriptase activity. Thus, in particularly preferred compositions the unit ratio of the reverse transcriptase enzymes to the DNA polymerase enzymes ranges from about 0.2:2 to about 500:2, preferably from about 0.5:2 to about 250:2 and most preferably a ratio of greater than 3:2. Of course, other suitable ratios of unit activities of reverse transcriptase enzymes to DNA polymerases suitable for use in the invention will be apparent to one of ordinary skill in the art.

Inhibition-Relieving Reagents

In accordance with the methods of the invention, one or more additional inhibition-relieving agents may optionally be added to the present compositions to assist in overcoming the inhibition of RT-PCR reactions by RTs such as M-MLV RT. Preferred inhibition-relieving agents for use in the present compositions include peptides, polypeptides and proteins such as (but not limited to) human serum albumin, bovine serum albumin, ovalbumin, Albumax, casein, gelatin, collagen, globulin, lysozyme, transferrin, myoglobin, hemoglobin, α-lactalbumin, fumarase, glyceraldehyde-3-phosphate dehydrogenase (GAPDH), amyloglucosidase, carbonic anhydrase, β-lactoglobulin, aprotinin, soybean trypsin inhibitor, trypsinogen, phosphorylase b, myosin, actin, β-galactosidase, catalase, tryptic soy digests, tryptose, lectins and the like, or fragments or derivatives thereof. Particularly preferred for use in the compositions and methods of the invention are bovine serum albumin, human serum albumin, Albumax and casein. Peptides, polypeptides or proteins are preferably added to the compositions to give a final concentration in the solution of about 0.01 to about 100 µg/ml, preferably about 0.1 to about 100 µg/ml, more preferably about 1 to about 50 µg/ml and most preferably about 2 to about 20 µg/ml.

dNTPs

The compositions of the invention further comprise one or more nucleotides (e.g., deoxynucleoside triphosphates (dNTPs)). The nucleotide components of the present compositions serve as the "building blocks" for newly synthesized nucleic acids, being incorporated therein by the action of the reverse transcriptases or DNA polymerases. Examples of nucleotides suitable for use in the present compositions include, but are not limited to, dUTP, dATP, dTTP, dCTP, dGTP, dITP, 7-deaza-dGTP, α-thio-dATP, α-thio-dTTP, α-thio-dGTP, α-thio-dCTP or derivatives thereof, all of which are available commercially from sources including Life Technologies, Inc. (Rockville, Md.), New England BioLabs (Beverly, Mass.) and Sigma Chemical Company (Saint Louis, Mo.). The dNTPs may be unlabeled, or they may be detectably labeled by coupling them by methods known in the art with radioisotopes (e.g., $^3$H, $^{14}$C, $^{32}$P or $^{35}$S), vitamins (e.g., biotin), fluorescent moieties (e.g., fluorescein, rhodamine, Texas Red, or phycoerythrin), chemiluminescent labels, dioxigenin and the like. Labeled dNTPs may also be obtained commercially, for example from Life Technologies, Inc. (Rockville, Md.) or Sigma Chemical Company (Saint Louis, Mo.). In the present compositions, the dNTPs are added to give a working concentration of each dNTP of about 10-1000 micromolar, about 10-500 micromolar, about 10-250 micromolar, or about 10-100 micromolar, and most preferably a concentration of about 100 micromolar.

Primers

In addition to nucleotides, the present compositions comprise one or more primers which facilitate the synthesis of a first DNA molecule complementary to all or a portion of an RNA template (e.g., a single-stranded cDNA molecule). Such primers may also be used to synthesize a DNA molecule complementary to all or a portion of the first DNA molecule, thereby forming a double-stranded cDNA molecule. Additionally, these primers may be used in amplifying nucleic acid molecules in accordance with the invention. Such primers include, but are not limited to, target-specific primers (which are preferably gene-specific primers), oligo(dT) primers, random primers or arbitrary primers. Additional primers that may be used for amplification of the DNA molecules according to the methods of the invention will be apparent to one of ordinary skill in the art.

Methods of RT-PCR

In the RT-PCR reaction, the reaction mixtures are incubated at a temperature sufficient to synthesize a DNA molecule complementary to all or portion of the RNA template. Such conditions typically range from about 20° C. to 75° C., more preferably from about 35° C. to 60° C. and most preferably from about 45° C. to about 55° C. After the reverse transcription reaction, the reaction is incubated at a temperature sufficient to amplify the synthesized DNA molecule. Preferably the amplification is accomplished via one or more polymerase chain reactions (PCRs). Preferred conditions for amplification comprise thermocycling, which may comprise alternating heating and cooling of the mixture sufficient to amplify the DNA molecule and which most preferably comprises alternating from a first temperature range of from about 90° C. to about 100° C., to a second temperature range of from about 45° C. to about 75° C., more preferably from about 50° C. to about 75° C. or from about 55° C. to about 75° C., and most preferably from about 65° C. to about 75° C. According to the invention, the thermocycling may be performed any number of times, preferably from about 5 to about 80 times, more preferably greater than about 10 times and most preferably greater than about 20 times.

The compositions and methods of the present invention may also be used for the production, analysis and quantitation of large nucleic acid molecules (e.g., by "long PCR" or "long RT-PCR"), preferably nucleic acid molecules that are larger than about 4-8 kilobases in size, more preferably larger than about 5-7 kilobases in size, and most preferably nucleic acid molecules that are larger than about 7 kilobases in size. In this aspect of the invention, combinations of DNA polymerases, preferably mixtures of one or more DNA polymerases lacking 3'-5' exonuclease activity (i.e., a "3' exo$^-$" polymerase) with one or more DNA polymerases having 3'-5' exonuclease activity (i.e., a "3' exo$^+$" polymerase), may be added to the compositions of the invention (see U.S. Pat. No. 5,436,149; see also co-pending U.S. patent application Ser. No. 08/801,720, of Ayoub Rashtchian and Joseph Solus, filed Feb. 14, 1997, and the co-pending U.S. patent application of Ayoub Rashtchian and Joseph Solus entitled "Stable Compositions for Nucleic Acid Amplification and Sequencing," filed Mar. 27, 1998, the disclosures of all of which are incorporated herein in their entireties). Preferred 3' exo$^-$ and 3' exo$^+$ polymerases for use in this aspect of the invention are thermostable 3' exo$^-$ and 3' exo$^+$ polymerases. Particularly preferred 3' exo$^-$ polymerases include, but are not limited to, Taq, Tne (exo$^-$), Tma (exo$^-$), VENT (exo$^-$)™, DEEPVENT (exo$^-$)™, Pfu (exo$^-$) and Pwo (exo$^-$) polymerases, or mutants, variants or derivatives thereof, which are preferably added to the compositions of the invention at a concentration in the solution of about 0.1-200 units per milliliter, about 0.1-50 units per milliliter, about 0.1-40 units per milliliter, about 0.1-36 units per milliliter, about 0.1-34 units per milliliter, about 0.1-32 units per milliliter, about 0.1-30 units per milliliter, or about 0.1-20 units per milliliter, and most preferably at a concentration of about 20 units per milliliter. Particularly preferred 3' exo$^+$ polymerases include, but are not limited to, VENT™, Pfu, Pwo, Tne, Kod and Tma, and most preferably DEEPVENT™, DNA polymerases, which should be added to the mixtures in sufficient quantity to give a final working concentration of about 0.0002-200 units per milliliter, about 0.002-100 units per milliliter, about 0.002-20 units per milliliter, about 0.002-2.0 units per milliliter, about 0.002-1.6 units per milliliter, about 0.002-0.8 units per milliliter, about 0.002-0.4 units per milliliter, or about 0.002-0.2 units per milliliter, most preferably at concentrations of about 0.40 units per milliliter. These thermostable DNA polymerases are available commercially, for example from Life Technologies, Inc. (Rockville, Md.), New England BioLabs (Beverly, Mass.), Finnzymes Oy (Espoo, Finland), Stratagene (La Jolla, Calif.), Boehringer Mannheim Biochemicals (Indianapolis, Ind.) and Perkin-Elmer Cetus (Norwalk, Conn.). The mixtures of the compositions of the invention and the 3' exo$^-$ and 3' exo$^+$ polymerases may be used in the methods of the invention to result in enhanced sensitivity of detection, and yield, of large RT-PCR products.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

Example 1

Inhibition of RT-PCR by RT

To examine inhibition of RT-PCR amplification by RT, CAT RNA was used as a template. RT-PCR reactions were conducted in a 50 µl final volume in PCR buffer (20 mM Tris-HCl, 50 mM KCl) or ELONGASE buffer (60 mM Tris-SO$_4$ (pH 9.1), 18 mM (NH$_4$)$_2$SO$_4$; total sulfur concentration approximately 23 mM) containing 20 units of M-MLV (H$^-$) RT, 1 mM dithiothreitol (DTT), 0.2 mM each of sense and antisense primers, 0.2 mM dNTPs, 1.25 mM MgCl$_2$, 2 units of Taq and various amounts of CAT mRNAs (0, 10, 10$^2$, 10$^3$, $10^4$, $10^5$, $10^6$ or $10^7$ copies per reaction). RT-PCR conditions were one cycle of 45° C. for 30 minutes and 94° C. for 2 minutes, followed by 40 cycles of 94° C. for 15 seconds/60° C. 30 seconds and then 72° C. for 5 minutes.

Upon analysis of the amplification products by 1.5% agarose gel electrophoresis (FIG. 1), significant-amplification of the 500 bp target sequence was observed in reactions carried out in ELONGASE buffer using $10^6$ or $10^7$ copies of CAT mRNA template (FIG. 1, lanes 8 and 9). In contrast, no significant PCR, product was observed for reactions carried out in standard PCR buffer at all template concentrations (FIG. 1, lanes 18, 19). These results indicate that the presence of RT in PCR reaction mixtures inhibits the amplification reaction, but that this inhibition is at least partially relieved using ELONGASE buffer.

Example 2

Role of Sulfur in Relief of RT Inhibition in PCR Amplification

To determine if the sulfate ion in ELONGASE buffer might be a key component for the relief of RT inhibition observed in Example 1, various reaction parameters such as pH, ionic conditions and buffer composition were studied in detail. RT-PCR reactions were carried out in a 50 µl final volume containing 1 mM DTT, 0.2 mM dNTPs, 1.5 mM MgSO$_4$, 0.2 mM each of sense and antisense human β-actin primers, 1 pg of total HeLa RNA template, 2 units of Taq DNA polymerase and 10 units M-MLV (H$^-$) RT in buffered salt solutions comprising various ionic and buffer conditions. RT PCR conditions were 30 minutes at 45° C. and 2 minutes at 94° C., followed by 40 cycles of 94° C. for 15 seconds/55° C. for 30 seconds/68° C. for 90 seconds, and one final extension for 5 minutes at 72° C. The ability to detect an amplified 1,026-bp RT-PCR product from 1 pg of total HeLa RNA was used as an assessment of the amplification success under the specific reaction conditions.

Upon analysis of 1,026-bp b-actin RT PCR products in 1% agarose gel electrophoresis, the results shown in Tables 1-7 were obtained.

Table 1: Compositions comprising Tris-HCl (pH 8.5-9.3) demonstrated a sensitivity of about 1 pg total HeLa RNA when 18 mM (NH$_4$)$_2$SO$_4$ was present. However, this increased sensitivity was obtained over a broader pH range (pH 7.8-9.3) when Tris-SO$_4$, buffer was used in place of Tris-HCl.

TABLE 1

Optimal pH in Tris-HCl and Tris-SO$_4$ Buffers.

| | pH | | | | | | | | |
|---|---|---|---|---|---|---|---|---|---|
| | 7.5 | 7.8 | 8.0 | 8.3 | 8.5 | 8.8 | 9.0 | 9.3 | 9.5 |
| Tris-HCl, 60 mM[1] | + | + | + | + | + | + | + | + | + |
| (NH$_4$)$_2$SO$_4$, 18 mM | + | + | + | + | + | + | + | + | + |
| Sensitivity (Yield of PCR Product) | − | − | − | − | + | − | ++ | + | − |
| Tris-SO$_4$, 60 mM | + | + | + | + | + | + | + | + | + |
| (NH$_4$)$_2$SO$_4$, 18 mM | + | + | + | + | + | + | + | + | + |
| Total Sulfur Concentration (mM)[2] | 41 | 38 | 35 | 32 | 30 | 26 | 23 | 22 | 21 |
| Sensitivity (Yield of PCR Product) | − | + | + | + | + | + | ++ | + | − |

[1]The pH in the Tris-HCl reaction mixture was adjusted using HCl. Therefore, no sulfur was contributed via pH adjustment, and the sulfur concentration for each pH tested was approximately 18 mM.
[2]The pH in the Tris-SO$_4$ reaction mixture was adjusted using sulfuric acid. Therefore, the addition of sulfuric acid increased the sulfur concentration to approximately that shown.

Table 2: In order to detect the 1,026-bp RT-PCR product in compositions comprising Tris-HCl buffer, the inclusion of 20 mM (NH$_4$)$_2$SO$_4$ in the compositions was essential. However, if Tris-SO$_4$ buffer (20-80 mM, pH 8.0-9.0) was used in place of Tris-HCl, the inclusion of (NH$_4$)$_2$SO$_4$ was not required.

TABLE 2

Requirement for Sulfur and Potassium.

| | pH | | | | | | | | | | | | | | | | | |
|---|---|---|---|---|---|---|---|---|---|---|---|---|---|---|---|---|---|---|
| | 9.0 | | | | | | 8.5 | | | | | | 8.0 | | | | | |
| Tris-HCl, 60 mM | + | + | + | + | + | + | + | + | + | + | + | + | + | + | + | + | + | + |
| (NH$_4$)$_2$SO$_4$, mM[1] | 0 | 10 | 20 | 40 | 60 | 80 | 0 | 10 | 20 | 40 | 60 | 80 | 0 | 10 | 20 | 40 | 60 | 80 |
| Sensitivity (Yield of PCR Product) | − | − | + | − | − | − | − | − | − | − | − | − | − | − | − | − | − | − |
| Tris-SO$_4$, mM | 20 | 40 | 60 | 80 | 100 | | 20 | 40 | 60 | 80 | 100 | | 20 | 40 | 60 | 80 | 100 | |
| KCl, 40 mM | + | + | + | + | + | | + | + | + | + | + | | + | + | + | + | + | |
| Total Sulfur Concentration (mM)[2] | 20 | 21 | 23 | 25 | 26 | | 22 | 26 | 30 | 34 | 38 | | 24 | 29 | 35 | 41 | 46 | |
| Sensitivity (Yield of PCR Product) | − | − | + | + | − | | + | + | + | + | − | | − | − | − | − | − | |

[1]The pH in the Tris-HCl reaction mixture was adjusted using HCl. Therefore, no sulfur was contributed via pH adjustment, and the sulfur concentration for each pH tested was approximately 18 mM.
[2]The pH in the Tris-SO$_4$ reaction mixture was adjusted using sulfuric acid. Therefore, the addition of sulfuric acid increased the sulfur concentration to approximately that shown.

Table 3: Requirement for sulfur for sensitive detection of 1,026 bp RT-PCR product was also demonstrated by use of taurine ($NH_2CH_2SO_3H$), which contains sulfur ion. Taurine relieved the RT-mediated inhibition of RT-PCR about as well as did ammonium sulfate.

TABLE 3

Requirement for Sulfur.

| Tris-HCl, 60 mM (pH 9.0) | + | + | + | + | + | + | + | + | + | + |
|---|---|---|---|---|---|---|---|---|---|---|
| [Taurine], mM | 0 | 10 | 20 | 40 | 60 | 0 | 0 | 0 | 0 | 0 |
| [Ammonium Sulfate], mM | 0 | 0 | 0 | 0 | 0 | 0 | 10 | 20 | 40 | 60 |
| Sensitivity (yield of PCR product) | − | + | ++ | +++ | +++ | − | ++ | +++ | − | − |

Table 4: The increased detection sensitivity of the Tris-$SO_4$ buffer system shown in Table 2 (60 mM, pH 8.5-9.0) could be further enhanced by the addition of 20-40 mM KCl, indicating that potassium-containing molecules not only were suitable substitutes for sulfur-containing molecules in the present compositions, but may also enhance the sensitivity of the RT-PCR reaction in their own right.

Table 5: Similar detection sensitivity and further enhancement by the addition of KCl was obtained in the Tris-taurine buffer system.

Table 6: The addition of $NH_4Cl$ in place of $(NH_4)_2SO_4$ in the present compositions did not relieve the RT-mediated inhibition of RT-PCR, indicating that sulfur-containing molecules are key components for the relief of RT inhibition in RT-PCR.

TABLE 6

Requirement for Sulfur.

| Buffer Composition (Additive to Tris-HCl, 60 mM) | Detection Sensitivity (Yield of PCR Product) | |
|---|---|---|
| | $(NH_4)_2SO_4$, 20 mM | $NH_4Cl$, 40 mM |
| Magnesium Sulfate, 1.5 mM | + | − |
| Magnesium Acetate, 1.5 mM | + | − |
| Magnesium Chloride, 1.5 mM | + | − |

Table 7: Requirement for sulfur ion for relief of RT-mediated inhibition of PCR was less stringent in Tris-acetate buffer systems than in Tris-sulfate buffer systems. In the Tris-acetate buffer system, RT-PCR products of 1,026 bp size were able to be observed even in the absence of sulfur ions.

TABLE 7

Requirement for Sulfur and Effect of Buffers.

| Tris-$SO_4$, 60 mM (pH 9.0) | + | + | + | + | + | − | − | − | − | − |
|---|---|---|---|---|---|---|---|---|---|---|

TABLE 4

Role of Potassium in Suboptimal Concentrations of Sulfur.

| | pH | | | | | | | | | | | | | | | | | |
|---|---|---|---|---|---|---|---|---|---|---|---|---|---|---|---|---|---|---|
| | 9.0 | | | | | | 8.5 | | | | | | 8.0 | | | | | |
| Tris-$SO_4$, 60 mM | + | + | + | + | + | + | + | + | + | + | + | + | + | + | + | + | + | + |
| $(NH_4)_2SO_4$, mM | 0 | 10 | 20 | 40 | 60 | 80 | 0 | 10 | 20 | 40 | 60 | 80 | 0 | 10 | 20 | 40 | 60 | 80 |
| Sensitivity (Yield of PCR Product) | − | − | ++ | − | − | − | − | + | + | − | − | − | − | − | − | − | − | − |
| Tris-$SO_4$, 60 mM | + | + | + | + | + | + | + | + | + | + | + | + | + | + | + | + | + | + |
| KCl, mM | 0 | 20 | 40 | 60 | 80 | 100 | 0 | 20 | 40 | 60 | 80 | 100 | 0 | 20 | 40 | 60 | 80 | 100 |
| Sensitivity (Yield of PCR Product) | − | − | + | + | + | − | − | − | +++ | +++ | − | − | − | − | − | − | − | − |

TABLE 5

Requirement for Sulfur and Potassium.

| [Tris-taurine], mM (pH 8.9) | 60 | 60 | 60 | 60 | 60 | 60 | 60 | 60 | 60 | 60 | 100 | 200 | 60 | 60 | 60 | 60 |
|---|---|---|---|---|---|---|---|---|---|---|---|---|---|---|---|---|
| [Ammonium sulfate], mM | 0 | 10 | 20 | 40 | 60 | 0 | 0 | 0 | 0 | 0 | 0 | 0 | 0 | 0 | 0 | 0 |
| [Taurine], mM | 0 | 0 | 0 | 0 | 0 | 0 | 0 | 0 | 0 | 0 | 0 | 0 | 10 | 20 | 40 | 60 |
| [KCl], mM | 0 | 0 | 0 | 0 | 0 | 0 | 10 | 20 | 40 | 60 | 0 | 0 | 0 | 0 | 0 | 0 |
| Sensitivity (yield of PCR product) | − | +++ | +++ | − | − | + | ++ | +++ | +++ | + | ++ | − | + | ++ | +++ | +++ |

TABLE 7-continued

Requirement for Sulfur and Effect of Buffers.

| Tris-acetate, 60 mM (pH 8.4) | − | − | − | − | − | + | + | + | + | + |
|---|---|---|---|---|---|---|---|---|---|---|
| [(NH$_4$)$_2$SO$_4$], mM | 0 | 10 | 20 | 40 | 80 | 0 | 10 | 20 | 40 | 80 |
| Sensitivity (yield of PCR product) | − | ++ | +++ | − | − | + | ++ | +++ | − | − |

Example 3

Role of Bovine Serum Albumin (BSA) in RT-PCR

To investigate other reaction components which might relieve the RT-mediated inhibition of RT-PCR, BSA was added to the present compositions. Compositions were formulated comprising increasing amounts of M-MLV (H$^−$) RT (from 10 units to 260 units) and various amount of BSA, and these compositions used in RT-PCR reactions. Reactions were conducted in a 50 µl final volume containing 60 mM Tris-SO$_4$ (pH 9.1), 18 mM (NH$_4$)$_2$SO$_4$, 0.2 mM dNTPs, 1.2 mM MgSO$_4$, 0.02 mM DTT, 0.2 mM each of human β-actin CAT mRNA sense and antisense primers, 2 units of Taq DNA polymerase and 100 pg of total HeLa RNA template for β-actin amplification, or 10$^5$ copies of total HeLa RNA template for CAT amplification. RT-PCR conditions were 30 minutes at 45° C. and two minutes at 94° C., followed by 40 cycles of 94° C. for 15 seconds/55° C. for 30 seconds/68° C. for 90 seconds, and then one final extension of five minutes at 72° C.

Figure 2A:
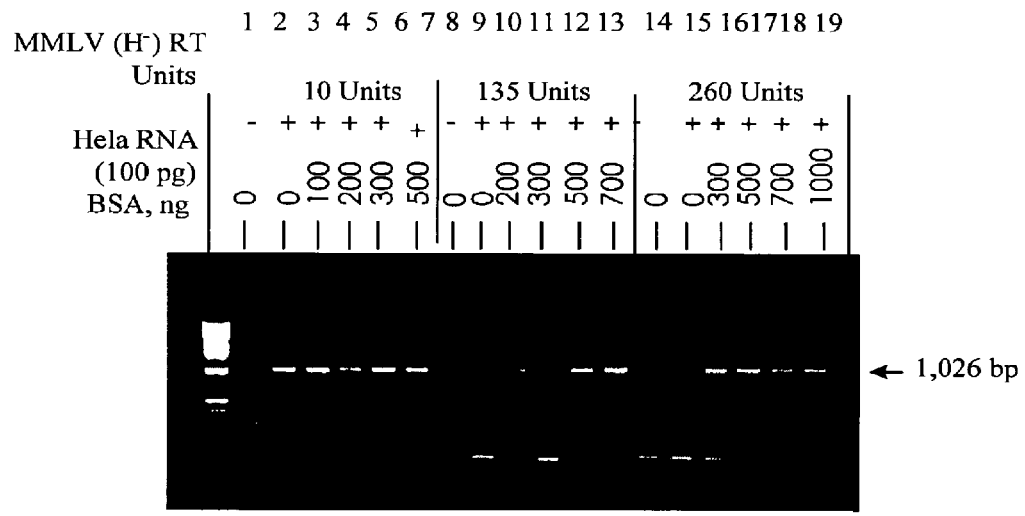
FIG. 2A is photograph of an EtdBr-stained gel demonstrating the protective role of bovine serum albumin (BSA) in RT-PCR of β-actin mRNA from 100 pg of HeLa total mRNA template. Lane 1 contains a DNA sizing ladder, and the arrow indicates the 1026 bp β-actin target sequence.
Figure 2B:
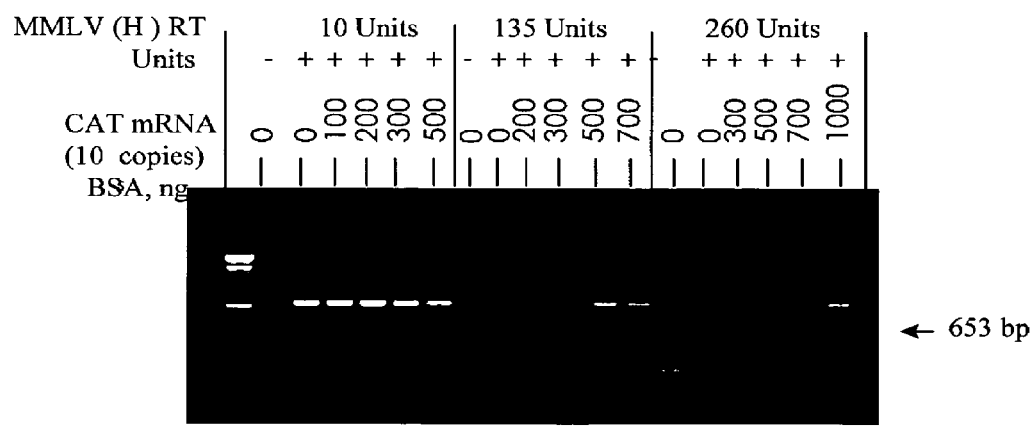
FIG. 2B is a photograph of an EtdBr-stained gel demonstrating the protective role of BSA in RT-PCR of CAT mRNA from $10^5$ copies of CAT mRNA template. Lane 1 contains a DNA sizing ladder, and the arrow indicates the 653 bp CAT target sequence.

Upon analysis of the 1,026-bp β-actin RT-PCR products in 1% agarose gel electrophoresis (FIG. 2A), RT inhibition was not observed with 10 units of RT, but increasing amounts of RT (135 units-260 units) inhibited RT-PCR completely. However, such RT inhibition was relieved by the addition of 200-1000 ng of BSA per reaction (i.e., a final BSA concentration of about 4-20 µg/ml). Similar results were obtained from the analysis of the 653-bp CAT RT-PCR products (FIG. 2B), where only a slightly higher amount of BSA (300-1000 ng per reaction i.e., a final BSA concentration of about 6-20 µg/ml) was required for the relief of RT inhibition. Together, these results indicate that the incorporation of proteins such as BSA into the compositions of the invention may assist in overcoming the inhibition of RT-PCR caused by RT.

Example 4

Performance of M-MLV, AMV, M-MLV (H$^−$) for RT-PCR in Sulfur- and BSA-Containing Buffer To study the performance of various RTs in RT-PCR, AMV-RT, M-MLV-RT, and M-MLV (H$^−$) RT were used in the present compositions. RT-PCR reactions for M-MLV-RT and M-MLV H$^−$RT (Superscript II) were conducted in a 50 µl final volume containing 60 mM Tris-SO$_4$ (pH9.1), 18 mM (NH$_4$)$_2$SO$_4$, 0.2 mM dNTPs, 250 ng BSA, 1.0 mM DTT, 0.2 mM each of CAT sense and antisense primers, 2 units of Taq DNA polymerase, 1.5 mM MgSO$_4$, and various amount of CAT RNA template (0, 10$^3$, 10$^4$ or 10$^5$ copies per reaction). The compositions containing AMV-RT were the same except that they lacked BSA. For each reaction, 5 units each of AMV-RT, M-MLV-RT or M-MLV (H$^−$) RT were used. RT-PCR cycling conditions were 30 minutes at 45° C. and 2 minutes at 94° C., followed by 40 cycles of 94° C. for 15 seconds/60° C. for 30 seconds, and then a final extension of five minutes at 72° C.

Figure 3:
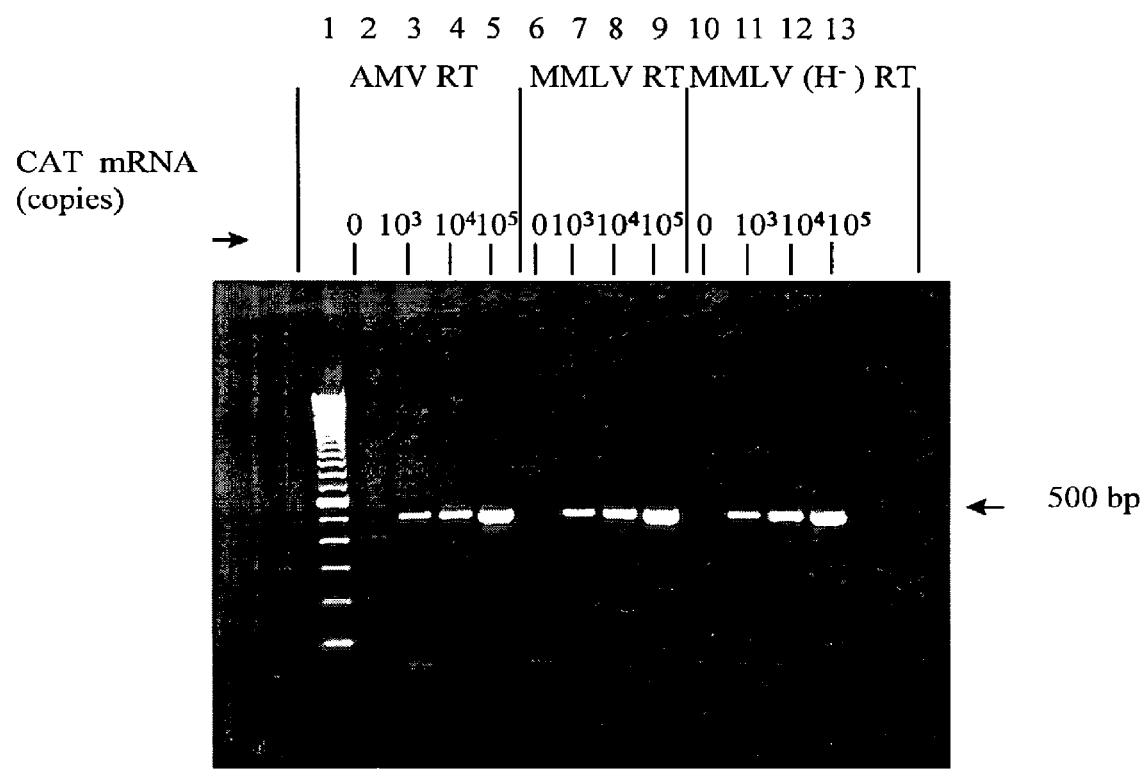
FIG. 3 is a photograph of an EtdBr-stained gel demonstrating the performance of various RTs in sulfate ion- or BSA-containing buffers. Lane 1: 100 bp DNA sizing ladder; Lanes 2-5: 5 units/reaction of AMV-RT; Lanes 6-9: 5 units/reaction of M-MLV-RT; Lanes 10-13: 5 units/reaction of M-MLV-RT (RNase H$^-$). Arrow indicates 500 bp CAT target sequence.

As shown in FIG. 3, upon analysis of 500-bp CAT RT-PCR products in 1.5% agarose gel electrophoresis the reactions performed with AMV-RT, M-MLV-RT, and M-MLV (H$^−$)-RT demonstrated efficient and sensitive RT-PCR product yield, with no inhibition of the RT-PCR reactions observed under any of the reaction conditions.

Example 5

RT-PCR Amplification of Long Nucleic Acid Templates

Having demonstrated the simplicity and sensitivity of the present methods in RT-PCR amplification of templates up to 3.5 kb in size, the efficacy of the invention in amplifying mRNAs up to 8.9 kb was examined.

Total HeLa RNA was isolated with TRIzol® Reagent (Life Technologies, Inc.; Rockville, Md.) and amplified as above. To examine possible temperature effects, identical reactions were assembled and incubated at 45° C. to 55° C. in duplicate. The total HeLa RNA used varied from 1 ng to 100 ng depending on the abundance of the mRNA. After the RT incubation for 30 minutes, the reactions were incubated at 94° C. for two minutes, followed by 40 cycles of 94° C. for 15 seconds, 55° C. for 30 seconds and 68° C. for 60 seconds, followed by a final 68° C. extension for five minutes.

For larger RT-PCR products, the magnesium concentration was increased to 1.8 mM from the standard 1.5 mM, and 1 µl of ELONGASE Enzyme Mix (Life Technologies, Inc.; Rockville, Md.) was added to each reaction. The final 50 µl reaction consisted of 1× ELONGASE buffer with 1.8 mM MgSO$_4$ and other salts, 200 µM of each dNTP, 2 µg/ml BSA, 0.2 µM of primers (GIBCO BRL Custom Primers; Life Technologies, Inc., Rockville, Md.), 100 ng of total HeLa RNA, 1 µl of the RT/Taq enzyme mix of the invention and 1 µl of ELONGASE Enzyme Mix. For the experiments using the same template of primers, a master mix of buffer, enzyme mixes, and primers or template was made to ensure consistency. The samples were incubated at 50° C. for 30 minutes and then 94° C. for two minutes. Amplification was performed with 40 cycles of 94° C. for 15 seconds, 58° C. for 30 seconds and 68° C. for six to nine minutes (one minute/kb). The RT-PCR products were resolved and visualized on 0.8 or 1.0% (w/v) agarose-TAE gels containing ethidium bromide.

Figure 4:
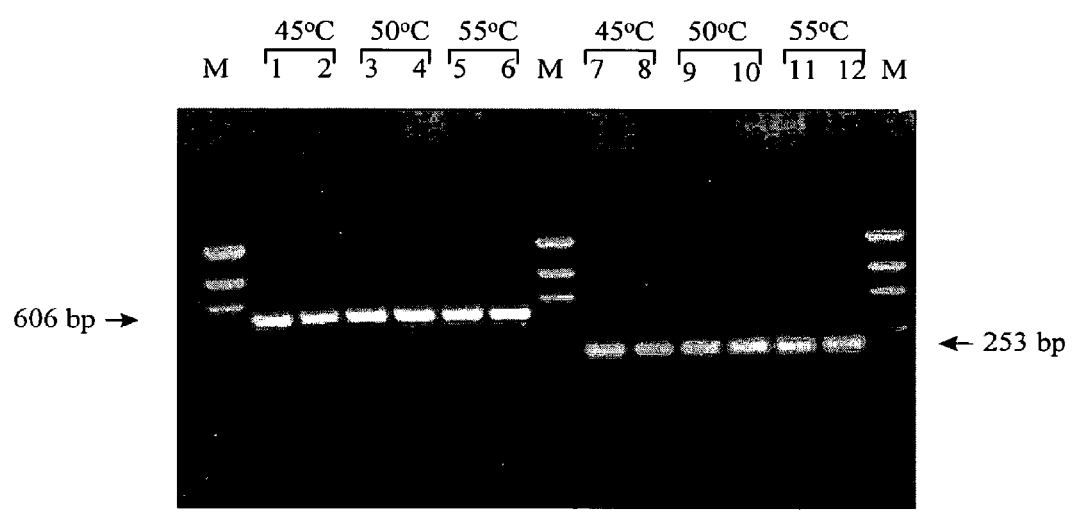
FIG. 4 is a photograph of an EtdBr-stained gel demonstrating the effect of reverse transcription reaction temperature on RT-PCR product formation. Duplicate samples of 100 ng (lanes 1-6) or 10 ng (lanes 7-12) of total HeLa RNA were reverse transcribed at the indicated temperatures, and a 606 bp DNA polymerase III ε subunit target sequence (lanes 1-6) or a 253 bp β-actin target sequence (lanes 7-12) were amplified by PCR. M: DNA sizing markers.
Figure 5:
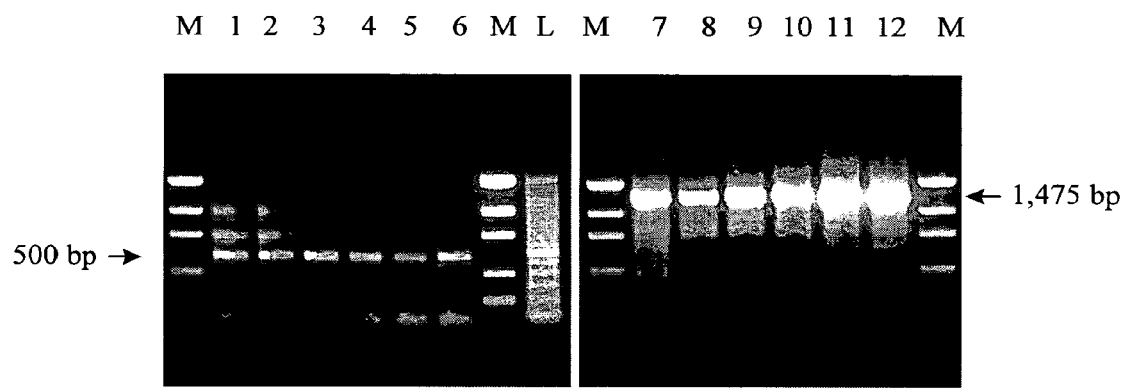
FIG. 5 is a photograph of an EtdBr-stained gel demonstrating improved yield of RT-PCR products obtained by conducting the RT reaction at higher temperatures. Duplicate samples of 10 ng of tobacco total RNA (lanes 1-6) or of 100 ng of total HeLa RNA (lanes 7-12) were reverse transcribed at 45° C. (lanes 1, 2, 7 and 8), 50° C. (lanes 3, 4, 9 and 10) or 55° C. (lanes 5, 6, 11 and 12), and a 500 bp GADPH target sequence (arrowhead; lanes 1-6) or a 1475 bp DNA polymerase III ε subunit target sequence (arrow; lanes 7-12) were amplified by PCR. M: DNA sizing markers; L: 100 bp nucleic acid sizing ladder.

Temperature of the RT reaction. SUPERSCRIPT II RT has improved temperature stability compared to M-MLV-RT (Gerard, G., et al., *FOCUS* 14:91 (1992)). To test the effect of temperature on RT-PCR products, 36 primer sets (representing different genes from human, rat, plant, and one in vitro transcript) were examined. As shown in FIG. 4, substantial product yield and specificity were observed at 45° C. for many of the fragments examined; increased incubation temperature did not result in increased yield or specificity. This result, however, was dependent upon the specific template and primer chosen (FIG. 5): for some template-primer combinations, the smearing of bands caused by mispriming that was characteristic of RT reactions conducted at 45° C. disappeared with increased temperature (FIG. 5; lanes 1-6), while in some cases a significant increase in product yield was observed when the RT reactions were conducted at elevated temperatures (FIG. 5; lanes 7-12).

Figure 6:
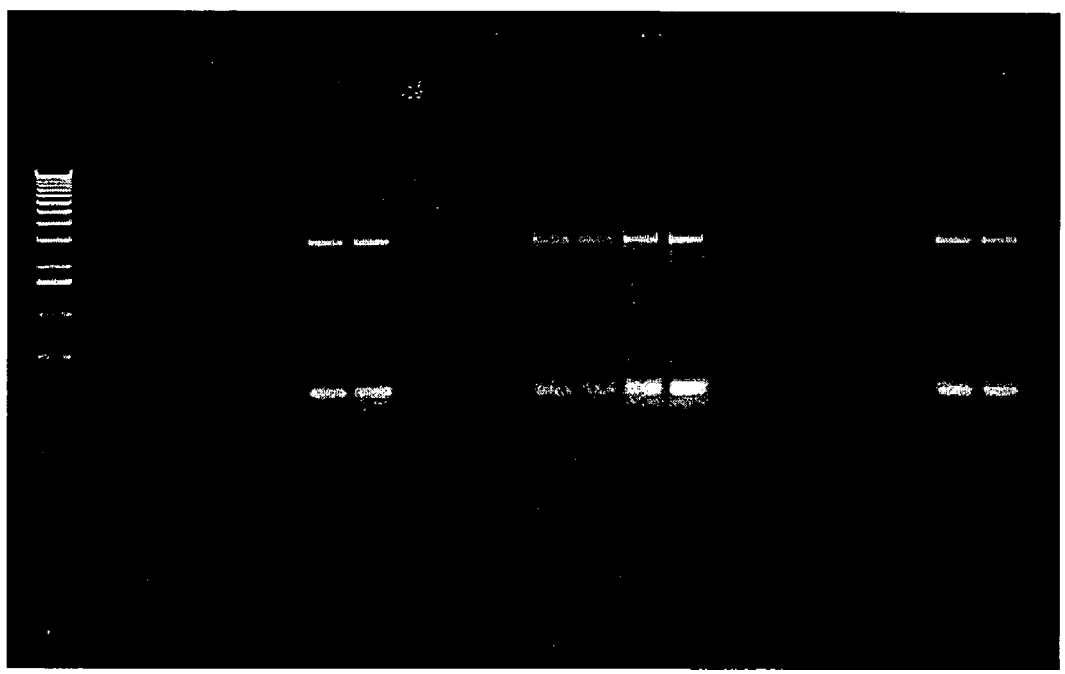
FIG. 6 is a photograph of an EtdBr-stained gel demonstrating the sensitivity and efficiency of the invention in RT-PCR of large (2-3 kb) products. A 2.78 kb tuberous sclerosis II fragment was amplified from varying amounts of total HeLa RNA that was reverse transcribed using the compositions of the invention without (lanes 1-6) or with (lanes 7-12) the addition of 1 μl of ELONGASE Enzyme Mix, or using a RT kit from Supplier A (lanes 13-18). Lanes 1, 2, 7, 8, 13 and 14: 1 ng of HeLa RNA; Lanes 3, 4, 9, 10, 15 and 16: 10 ng of HeLa RNA; Lanes 5, 6, 11, 12, 17 and 18: 100 ng of HeLa RNA; M: DNA sizing markers.

Long RT-PCR Products. For studies of full-length coding sequences or for amplification of long segments of RNA, the use of the compositions of the present invention supplemented with ELONGASE Enzyme Mix was tested. As shown in FIG. 6, the present system and Supplier A's kit were able to amplify a 2.8-kb product from 100 ng, but not from 10 ng, of total RNA. The addition of ELONGASE Enzyme Mix to the present system not only increased the product yield with 100 ng of total RNA, but also increased the sensitivity to allow amplification of long templates from 10 ng total RNA (FIG. 6; lanes 7-12). In contrast, Supplier A's kit was not able to amplify the 2.8-kb target from 10 ng of total RNA (FIG. 6; lanes 13-18) even though it contained a polymerase enzyme mix designed for long templates.

Figure 7:
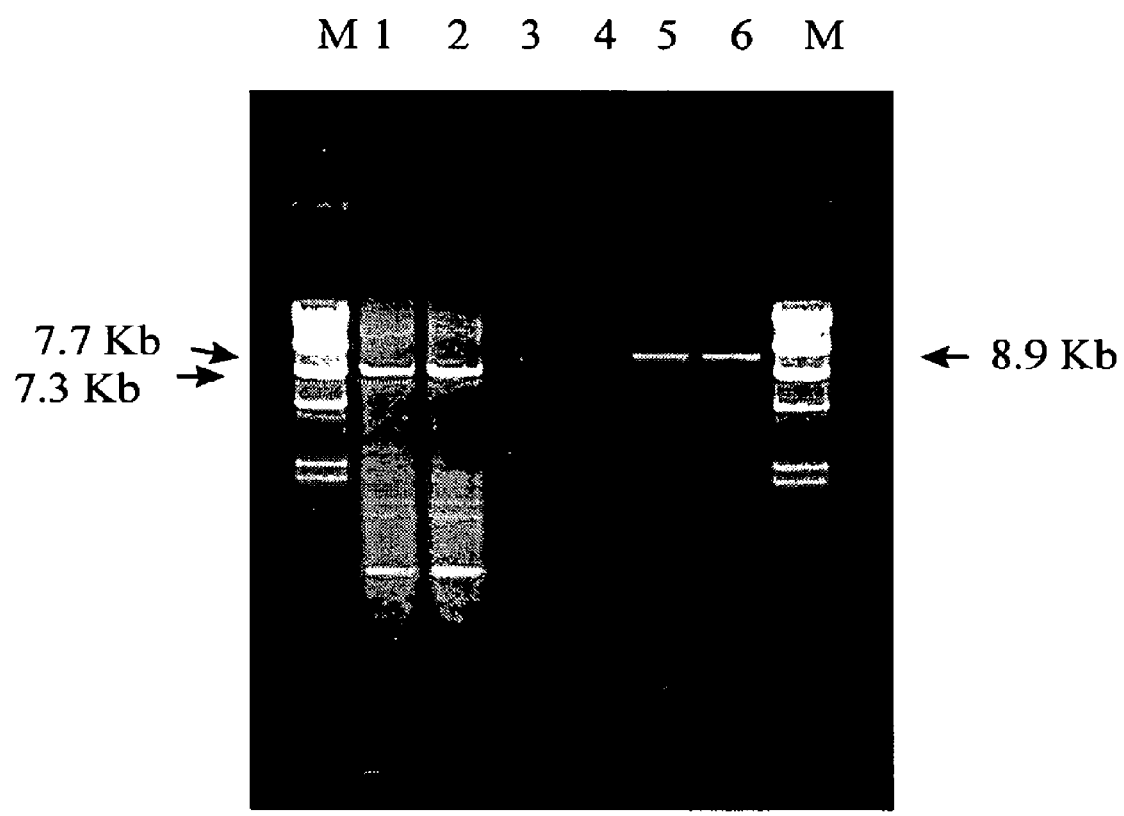
FIG. 7 is a photograph of an EtdBr-stained gel demonstrating the sensitivity and efficiency of the invention in RT-PCR of long (>3 kb) products. 100 ng of total HeLa RNA was reverse transcribed using the compositions of the invention with the addition of 1 μl of ELONGASE Enzyme Mix, and fragments of the adenomatous polyposis coli gene that were 7.3 kb (lanes 1, 2), 7.7 kb (lanes 3, 4) or 8.9 kb (lanes 5, 6) in size were amplified by PCR. M: DNA sizing markers (HindIII digest of λ DNA).

The compositions and methods of the invention were also found to be useful in amplifying large (>3-5 kb) RT-PCR products. As shown in FIG. 7, the compositions of the present invention, when supplemented with ELONGASE Enzyme Mix, produced RT-PCR products up to 8.9 kb in size. The ladder of bands observed upon amplification with these compositions is not uncommon for long RT-PCR, and the variation in product yields may be partially due to the use of different primer sets. These results demonstrate that the addition of ELONGASE Enzyme Mix to the present compositions makes it possible to amplify long and rare mRNAs directly from total RNA preparations by the methods of the invention. Further, the thermostability of SUPERSCRIPT II RT, facilitating RT-reactions at temperatures of up to 55° C., can increase the specificity and product yield for some templates and primer sets.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for amplifying a nucleic acid molecule comprising:
    (a) first, contacting an RNA template with a mixture comprising a Moloney murine leukemia virus (M-MLV) reverse transcriptase and one or more DNA polymerases, thereby forming a reaction mixture that comprises the RNA template, the reverse transcriptase and the one or more DNA polymerases, wherein the unit ratio of said reverse transcriptase to said DNA polymerases in the reaction mixture is greater than about 3:2
    (b) second, incubating said reaction mixture under conditions sufficient to reverse transcribe the RNA template; and
    (c) third, further incubating the reaction mixture under conditions sufficient to amplify a DNA molecule complementary to all or a portion of said RNA template.

2. The method of claim 1, wherein said mixture further comprises one or more nucleotides.

3. The method of claim 2, wherein said nucleotides are deoxyribonucleoside triphosphates or derivatives thereof, or dideoxyribonucleoside triphosphates or derivatives thereof.

4. The method of claim 2, wherein said deoxyribonucleoside triphosphates are selected from the group consisting of dATP, dUTP, dTTP, dGTP, and dCTP.

5. The method of claim 1, wherein said mixture further comprises one or more oligonucleotide primers.

6. The method of claim 1, wherein said reverse transcriptase is substantially reduced in RNase H activity.

7. The method of claim 1, wherein said one or more DNA polymerases are thermostable DNA polymerases.

8. A method for one-step RT-PCR, said method comprising:
    (a) first, contacting an RNA template with a mixture comprising a Moloney murine leukemia virus (M-MLV) reverse transcriptase and one or more DNA polymerases, thereby forming a reaction mixture that comprises the RNA template, the reverse transcriptase and the one or more DNA polymerases,
    (b) second, incubating said reaction mixture under conditions sufficient to reverse transcribe the RNA template; and
    (c) third, further incubating the reaction mixture under conditions sufficient to amplify a DNA molecule complementary to all or a portion of said RNA template.

9. The method of claim 8, wherein the unit ratio of said reverse transcriptase to said one or more DNA polymerases is greater than 3:2.

10. The method of claim 8, wherein said M-MLV is substantially reduced in RNase H activity.

11. The method of claim 8, wherein said one or more DNA polymerases is selected from the group consisting of Tne, Tma, Taq, Pfu, Tth, VENT, DEEPVENT, Pwo, Ttl, and mutants, variants and derivatives thereof.

12. The method of claim 8, wherein said mixture comprises one or more sulfur-containing molecules.

13. The method of claim 8 or 12, wherein said mixture comprises one or more acetate-containing molecules.

14. The method of claim 8 or 12, wherein said mixture comprises one or more potassium-containing molecules.

* * * * *